(12) United States Patent
Hinderer et al.

(10) Patent No.: US 8,703,123 B2
(45) Date of Patent: Apr. 22, 2014

(54) METHOD FOR OBTAINING BIOLOGICALLY ACTIVE RECOMBINANT HUMAN G-CSF

(75) Inventors: Walter Hinderer, Rodgau (DE); Christian Scheckermann, Ehrenkirchen (DE)

(73) Assignee: BioGeneriX GmbH, Ulm (DE)

( * ) Notice: Subject to any disclaimer, the term of this patent is extended or adjusted under 35 U.S.C. 154(b) by 0 days.

(21) Appl. No.: 13/634,801

(22) PCT Filed: Mar. 17, 2011

(86) PCT No.: PCT/EP2011/001331
§ 371 (c)(1),
(2), (4) Date: Sep. 13, 2012

(87) PCT Pub. No.: WO2011/113601
PCT Pub. Date: Sep. 22, 2011

(65) Prior Publication Data
US 2012/0328560 A1    Dec. 27, 2012

(30) Foreign Application Priority Data

Mar. 17, 2010 (EP) .................................. 10002811

(51) Int. Cl.
| | | |
|---|---|---|
| A61K 35/00 | (2006.01) | |
| C07K 1/16 | (2006.01) | |
| C07K 1/18 | (2006.01) | |
| C07K 1/20 | (2006.01) | |

(52) U.S. Cl.
USPC ............ 424/124; 530/351; 530/416; 530/417

(58) Field of Classification Search
None
See application file for complete search history.

(56) References Cited

U.S. PATENT DOCUMENTS 7,306,931 B2 * 12/2007 Rosendahl et al. .......... 435/69.1

FOREIGN PATENT DOCUMENTS

| EP | 1 630 173 A2 | 3/2006 | |
|---|---|---|---|
| EP | 1 630 173 A3 | 3/2006 | |
| EP | 1 837 346 A2 | 9/2007 | |
| EP | 1837346 | * 9/2007 | ........... C07K 14/535 |
| EP | 1 837 346 A3 | 10/2007 | |
| WO | WO 2007/009950 A1 | 1/2007 | |
| WO | WO 2008/096370 A2 | 8/2008 | |
| WO | WO 2008/096370 A3 | 8/2008 | |

OTHER PUBLICATIONS

Rainer et al., In vitro inclusion body proteins, FASEB J. 10, 49-56, 1996.*
English translation of body of EP1630173, originally publihed Mar. 1, 2006 in German.*
English translation of claims of EP1630173, originally publihed Mar. 1, 2006 in German.*
Rao Dasari et al. (2008). Optimization of the downstream process for high recovery of rhG-CSF from inclusion bodies expressed in *Escherichia coli. Process Biochemistry*, 43(5), 566-575.
Chen et al. (2009). Cooperative effects of urea and l-arginine on protein refolding. *Protein Expression and Purification* 66(1), 82-90.
Schwanke et al. (2009). Molecular cloning, expression in *Escherichia coli* and production of bioactive homogeneous recombinant human granulocyte and macrophage colony stimulating factor. *International Journal of Biological Macromolecules*, 45(2), 97-102.
International Search Report, mailed May 12, 2011 in connection with PCT International Application No. PCT/EP2011/001331, filed Mar. 17, 2011.

* cited by examiner

*Primary Examiner* — Elly-Gerald Stoica
(74) *Attorney, Agent, or Firm* — John P. White; Cooper & Dunham LLP

(57) ABSTRACT

Provided is a method of obtaining biologically active recombinant human G-CSF from inclusion bodies, wherein the solubilization and refolding process can be performed at ambient temperature and the purification step comprises reversed phase chromatography (RP), in particular RP-HPLC. The G-CSF preparation so obtained is characterized by high purity and homogeneity.

17 Claims, 3 Drawing Sheets

METHOD FOR OBTAINING BIOLOGICALLY ACTIVE RECOMBINANT HUMAN G-CSF

CROSS-REFERENCE TO RELATED APPLICATIONS

This application is a §371 national stage of PCT International Application No. PCT/EP2011/001331, filed Mar. 17, 2011, claiming priority of European Patent Application No. 10 002 811.7, filed Mar. 17, 2010, the contents of each of which are hereby incorporated by reference in their entirety.

FIELD OF THE INVENTION

The present invention relates to a procedure for the production of granulocyte-colony stimulating factor (G-CSF), in particular recombinant human G-CSF (rhG-CSF) in a highly active and pure form. This is achieved by refolding solubilized G-CSF contained in inclusion bodies in an appropriate redox system at ambient temperatures and using at least one reversed phase (RP) chromatography step in the purification process.

BACKGROUND TO THE INVENTION

G-CSF (granulocyte-colony stimulating factor) is a hematopoietic cytokine, released mainly by mononuclear cells and fibroblasts, that stimulates the proliferation and differentiation of precursor cells of the granulocyte lineage and the activation of functionally mature neutrophils. Due to said characteristics, G-CSF has come to be used in different medical fields, like for example in the reconstitution of normal blood cell populations subsequent to chemotherapy or irradiation or for stimulating the immune response to infectious pathogens. Thus in the clinics, G-CSF is mainly employed in anti-tumor therapy, particularly in the treatment of neutropenia as a consequence of chemotherapy, and is furthermore used in bone marrow transplantations and in the treatment of infectious diseases. The first commercially available G-CSF preparation based on recombinant G-CSF was produced and distributed by Amgen under the trade name Neupogen®.

Human G-CSF in its naturally occurring form is a glycoprotein having a molecular weight of about 20,000 Dalton and five cysteine residues. Four of these residues form two intramolecular disulfide bridges, which are of essential importance for the activity of the protein. Recombinant forms of G-CSF are mainly used for producing pharmaceuticals, which can for example be obtained by means of expression in mammalian cells like CHO (Chinese Hamster Ovary) cells or in prokaryotic cells like *E. coli*. When recombinant proteins are expressed in prokaryotes the proteins are often produced within the host cell in the form of at least partially inactive, insoluble aggregates (refractile bodies, inclusion bodies IB). Before such proteins can be used they have to be converted into their active form.

The formation of said inclusion bodies leads to the necessity of solubilizing and renaturing the proteins subsequent to isolation of the inclusion bodies by means of centrifugation at moderate speed with the aid of suitable means in order to maintain their active configuration.

Processes for the renaturation of recombinant proteins derived from inclusion bodies are generally known and described for example in EP 0 114 506, WO 84/03711, U.S. Pat. No. 4,530,787 and EP 0 241 022. In addition, general techniques relating to solubilization and renaturing of denatured proteins have been described in EP 0 512 097, EP 0 364 926, EP 0 219 874 and WO 01/87925 and can furthermore be taken from scientific literature and standard works on protein chemistry.

EP 0 500 108 describes a method for activating human recombinant G-CSF in an inactive form from inclusion bodies using a reduced glutathione (GSH) and oxidized glutathione (GSSH) redox shuffling system and analysis of reactivation kinetics for G-CSF under certain conditions. However, a downstream purification process is not disclosed.

In EP 0 719 860, G-CSF containing inclusion bodies were solubilized with N-Lauroylsarcosine (sarcosyl) and subsequently refolding was achieved by air-oxidation using copper sulfate. The disadvantages of this method are side reactions, e.g., formation of superoxide radicals on amino acid side chains. Furthermore, the refolding process is time consuming and it is difficult to obtain standardized refolding parameters. Finally, removal of the denaturant including a chromatographic step leads to a loss of about 20% of total protein yield. The G-CSF obtained is subsequently purified by an anion exchange chromatography and a cation exchange chromatography.

EP 1 630 173 and EP 1 837 346 describe methods of obtaining human recombinant G-CSF from inclusion bodies using a reduced glutathione (GSH) and oxidized glutathione (GSSH) redox shuffling system, wherein the refolding step is performed at low temperatures for more than half a day. Therefore, at an industrial scale this process is energy and thus cost consuming due to cooling large volumes of protein solution over many hours. The resulting G-CSF is subsequently purified by cation exchange chromatography.

In WO2007/009950 the method for purification of G-CSF taught in EP 1 630 173 is further specified with respect to the chromatographic steps in that cation exchange chromatography and hydrophobic interaction chromatography are consecutively performed without any intermediate step in between. In particular, the chromatographic purification procedure comprises a sequence of two cation exchange chromatography steps conducted before and after the hydrophobic interaction chromatography, respectively.

However, while means and methods for providing purified G-CSF at therapeutic grade were known in the prior art, processes available to date for obtaining G-CSF from inclusion bodies, in particular at a commercial scale are generally time-, labor- and cost-consuming. This technical problem is solved by the embodiments as characterized in the claims and described further below. In addition, as described further below, these embodiments provide for separation of a conformational G-CSF isoform and, therefore, a highly homogeneous G-CSF preparation.

SUMMARY OF THE INVENTION

The present invention provides a method for recovering and purifying granulocyte-colony stimulating factor (rhG-CSF) from a G-CSF producing recombinant cell. Said method comprises solubilizing the recombinant protein from inclusion bodies, refolding the G-CSF molecule by simply diluting the solubilizate within a refolding buffer at moderate temperatures preferably >10° C. and purifying the refolded G-CSF by chromatography, wherein at least one chromatography step comprised a reversed phase (RP) chromatography. This method is generally characterized by (a) solubilizing the G-CSF contained in the inclusion bodies with a solubilization buffer containing a denaturing agent and a reducing agent, (b) refolding the G-CSF by diluting the solubilizate with a refolding buffer containing reduced and oxidized glutathione at a temperature >10° C.; and (c) purifying the refolded G-CSF by at least one chromatography step, preferably comprising reversed phase (RP) chromatography.

In particular, in one aspect the present invention is based on a refolding process in a suitable redox system conducted at temperatures above 10° C. within less than half a day and advantageously at room temperature, i.e. at 20±2° C. within 3 to 4 hours. Besides the fact that efficient and accurate renaturation of G-CSF molecules can be achieved under these conditions, the drawbacks of previous methods described in the prior art referenced above can be avoided. Thus, the method of the present invention is easy to perform, less time consuming and does not involve energy consuming cooling systems.

Furthermore, the method of the present invention is based on the surprising observation that during the procedure of producing and recovering G-CSF, at least one G-CSF isoform is formed which became only visible by applying an analytical reversed phase-high pressure liquid chromatography (RP-HPLC) at 60° C.; see FIG. 3, revealing a slightly lower hydrophobicity than the main form. The structural nature of this additional misfolded isoform of G-CSF was investigated in detail and further characterized as described below. The maximum content of the additional G-CSF isoform in the whole preparation could made up to 7% of the total G-CSF protein yield. Detailed analysis using CD spectroscopy revealed that the G-CSF isoform differs from the subject G-CSF reference in a higher content of α-helical structures (66% for the isoform and 52% for the G-CSF reference). One characteristic feature of this additional isoform is its lower hydrophobicity in comparison to a G-CSF reference standard and the main fraction of the G-CSF preparation of the present invention, for which reason it can be separated and thus almost entirely excluded from the preparation. As a result the incorporation of the RP chromatography step and in particular RP-HPLC as a process step within the method of the present invention leads to an improved, i.e., highly purified G-CSF preparation which is substantially free of this isoform and further product-related impurities, i.e., the less hydrophobic G-CSF isoform content remains below 1% of total G-CSF protein. In this context, RP chromatography is to be distinguished from hydrophobic interaction chromatography (HIC) that is not a preferred embodiment of the method according to the present invention. Hence, with respect to the purification of G-CSF, RP and RP-HPLC, respectively, has hitherto been only employed for analytical purposes; see, e.g., WO2007/009950. The mentioned chromatography principles are also definitely distinguished among experts (see, for example, Bioanalytik, F. Lottspeich, H. Zorbas (ed.), Heidelberg, Berlin, Germany, Spektrum Akad. Verlag 1998). For example, while HIC is typically water-eluted, RP is solvent-eluted, wherein elution is done with a gradient to higher concentrations of solvent such as acetonitrile or ethanol. Preferably, the chromatographic steps comprise RP-high pressure liquid chromatography (HPLC) under appropriate conditions, preceded by an application of a cation exchange (CEX) chromatography.

In this context, it is prudent to assume that in the methods of the prior art for obtaining G-CSF from inclusion bodies isoforms of G-CSF are formed as well but hitherto have not been detected since under the conditions of the analytical RP-HPLC used in the prior art the isoforms were not apparent. Furthermore, since the existence of such G-CSF isoforms was not known there was no reason to look for.

Accordingly, the method of the present invention, in particular the preparative RP chromatography step and RP-HPLC step, respectively, may be implemented in purification processes for G-CSF, especially G-CSF obtained from inclusion bodies after solubilization/renaturation in a suitable redox system such as those described in the documents referred to above. Moreover, in combination with a preceding cation exchange (CEX) chromatography step, these two chromatography steps are sufficient to purify human recombinant G-CSF at a grade that is sufficient to use the resultant G-CSF as a drug. Thus, though the method of the present invention may be preferably carried out as outlined in FIG. 1 and illustrated in the Examples, the person skilled in the art will acknowledge that in order to arrive at a G-CSF with a therapeutic grade, performing CEX chromatography and a subsequent RP-HPLC is sufficient while any other purification steps may be altered or omitted at all.

In summary, a method of obtaining pure biologically active human recombinant G-CSF is provided that can be conducted with a minimum of manufacturing process steps keeping technical complexity as well as energy costs at a low level, and wherein the resultant G-CSF preparation is substantially similar to commercially available reference products and devoid of additional isoforms of G-CSF.

The G-CSF preparation obtained in accordance with the method of the present invention is thus advantageous in comparison with those obtained in accordance with methods of the prior art which do not utilize a RP-HPLC chromatography in terms of purity, i.e. in being more homogeneous in its G-CSF protein molecules. Moreover, due to the homogeneity of the G-CSF preparation of the present invention it is prudent to expect that the in vivo activity of the G-CSF preparation of the present invention is at least similar if not improved to the recombinant G-CSF products hitherto commercially available. This also implies that pharmacokinetic and pharmacodynamic properties otherwise will be similar to the ones of market products. The G-CSF obtained in accordance with the method of the present invention is thus particularly suitable for use in human medicine.

In addition, the G-CSF preparation of the present invention is particularly suited for further derivatization since the thus chemically modified product retains the high purity and homogeneity of the G-CSF preparation. Therefore, in a further embodiment, the method of the present invention further comprises chemical modification of the G-CSF obtained in accordance with the said method, for example by covalently attaching a water-soluble polymer to the G-CSF such as polyethylene glycol (PEG).

Furthermore, in view of the above considerations the present invention concerns a method for the production of a pharmaceutical composition of recombinant G-CSF or a derivative thereof and pharmaceutically acceptable additives such as buffers, salts and stabilizers, wherein said method comprises the method for obtaining G-CSF as disclosed herein and in particular in the Examples. Preferably, the purified biologically active G-CSF or derivative thereof, e.g. pegylated G-CSF is formulated in 10 mM acetic acid at a pH of 4.0, 0.0025% Polysorbate 80 and 50 g/l Sorbitol. Pharmaceutical compositions so obtained are also subject of the present invention.

(a) Fermentation and Harvesting
  a. Culturing rhG-CSF producing recombinant cells, which over-expressed rhG-CSF accumulating in high density in inclusion bodies;
  b. Isolation of inclusion bodies;
  c. Solubilization of inclusion bodies by the use of a reducing agent in a denaturation buffer followed by filtration;
  d. Refolding achieved by supplying a refolding buffer and transferring solubilization mixture into said refold buffer in a single step dilution process, wherein a redox-system based on oxidized and reduced glutathione (GSII/GSSH) is used in a weak alkali arginine-hydrochloride buffer and incubating at temperatures above 10° C. for at least three hours to generate biologically active soluble rhG-CSF in a stainless steel-tank followed by filtration;
(b) Purification of Soluble rhG-CSF
  a. Ultra- and diafiltration step for exchanging the buffer, reducing the concentration of the denaturant and concentrating the refolded G-CSF, preferably by using a pore size of MWCO 10 kDa and followed by filtration;
  b. Cation exchange chromatography for removing aggregated species as well as host proteins and DNA, exchanging the buffer, and concentrating the G-CSF fraction via volume reduction;
  c. A microfiltration step to remove insoluble impurities;
  d. A RP-HPLC purification step under suitable conditions at ambient temperatures performed by for example a Jupiter C4, in order to remove the less hydrophobic G-CSF isoform which elutes prior to the main fraction of G-CSF; and removing oxidized and reduced derivates of G-CSF
  e. An ultra- and diafiltration step (e.g. tangential flow filtration) for concentrating purified G-CSF and adjusting G-CSF into desired formulation, preferably by using a pore size of MWCO 5 kDa and followed by filtration;
  f. storage of purified G-CSF at preferably 2-8° C.

The individual process and purification steps are further explained in the description and examples.

Figure 2:
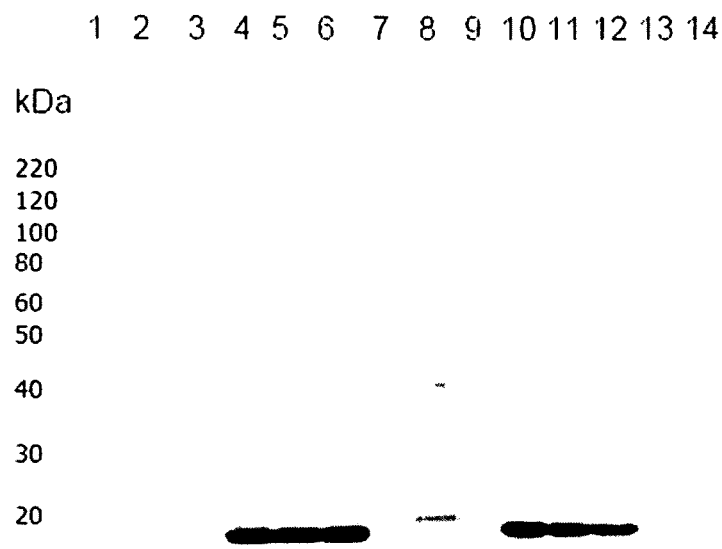

FIG. 2: Western blot analysis of purified rhG-CSF isolated from inclusion bodies. Purified G-CSF proteins were separated by 4-20% Tris-Glycine SDS-PAGE and blotted. The Western blot was incubated with primary anti-G-CSF antibody and developed using a secondary reporter antibody. Each 0.1 µg protein were loaded per slot. 3, 7, 9 and 13, empty lanes; 2, 8 and 14, molecular weight marker (Magic Mark XP); 4-6, G-CSF obtained by the method as illustrated in the Examples; 10-12, Neupogen® as reference. Neupogen® and G-CSF run at approximately 18 kDa as depicted in lanes 4-6 compared to lanes 10-12. As a result, G-CSF obtained according to the method of the present invention is apparently lacking additional bands and is comparable to Neupogen®.

Figure 3:
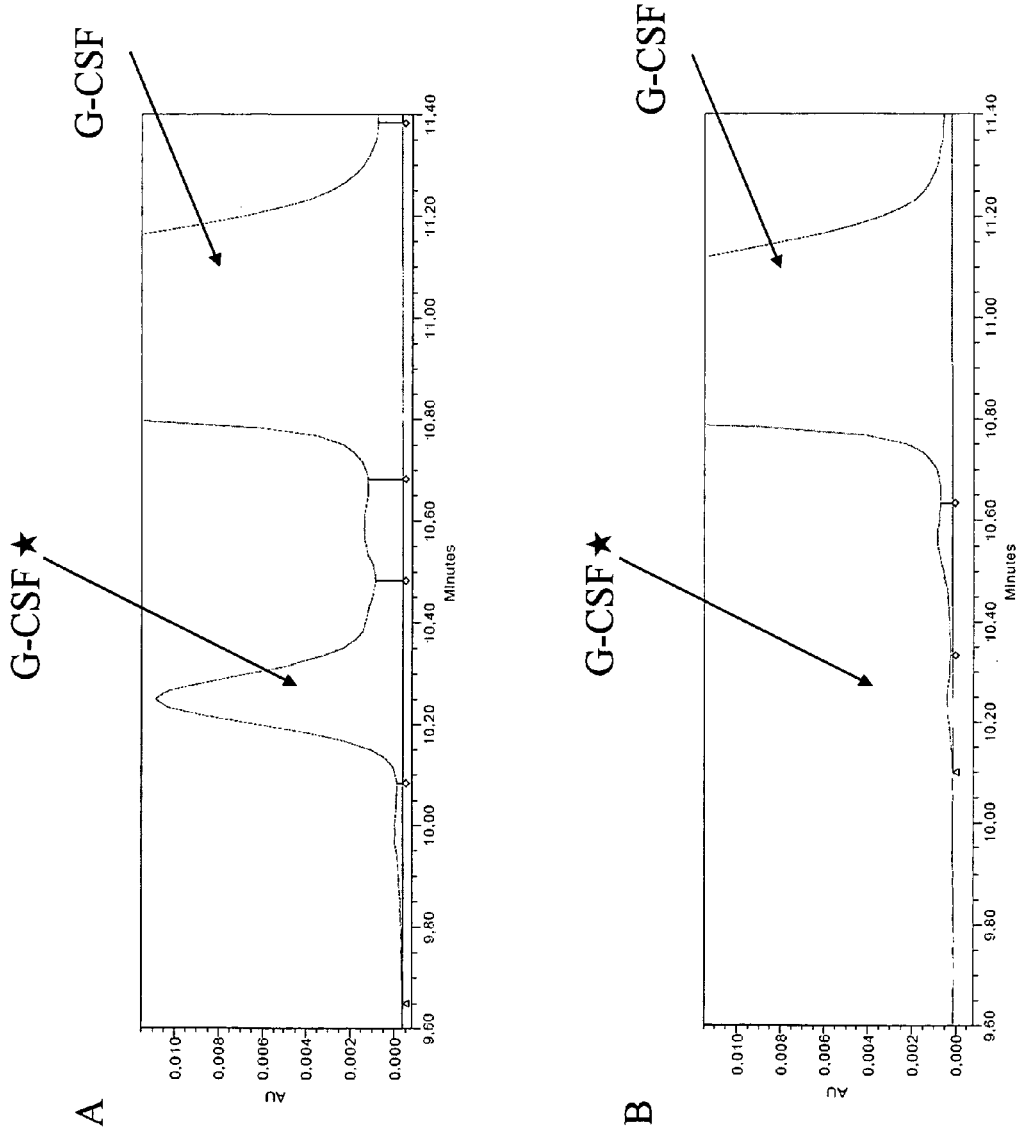

FIG. 3: Analytical RP-HPLC analysis of rhG-CSF preparation before or after the RP-HPLC preparative purification step according to the method of the present invention. After refolding and purification by CEX chromatography, G-CSF samples were taken before (A) or after (B) RP-HPLC preparative chromatography purification step and subjected to analytical RP-HPLC analysis at 60° C. in order to determine the composition of the samples. G-CSF ★ denotes the less hydrophobic isoform of G-CSF, whereas G-CSF designates the main fraction. Note, in (A) with the sample taken before the RP-HPLC purification step, an additional peak prior to the main fraction peak is visible (arrow). In (B) with the sample taken after the RP-HPLC purification step, the main peak is visible, whereas the second peak corresponding to the less hydrophobic G-CSF isoform highlighted in (A) by an arrow is almost completely missing.

DETAILED DESCRIPTION OF THE INVENTION

The present invention generally concerns a method for the large-scale production of a highly purified and homogeneous G-CSF preparation with minimized amounts of a less hydrophobic isoform of G-CSF compared to a reference G-CSF. More specifically, the present invention relates to a method of obtaining G-CSF from a G-CSF producing recombinant cell such as *E. coli* comprising solubilization of the recombinant G-CSF protein from inclusion bodies, refolding the G-CSF molecule by diluting the solubilizate within a refolding buffer at ambient temperatures, preferably >10° C., and purifying the refolded G-CSF by chromatography, wherein at least one chromatography step comprises reversed phase (RP) chromatography. In other words, the method of the present invention relates to a method for obtaining biologically active human G-CSF from inclusion bodies comprising the steps:
(a) solubilizing the G-CSF contained in the inclusion bodies with a solubilization buffer containing a denaturing agent and a reducing agent;
(b) refolding the G-CSF by diluting the solubilizate with a refolding buffer containing reduced and oxidized glutathione at a temperature >10° C.; and
(c) purifying the refolded G-CSF by at least one chromatography step comprising reversed phase (RP) chromatography.

According to the present invention, the term "biologically active human G-CSF" is understood to denote a G-CSF preparation, which has been purified by the method according to the present invention and is capable of enhancing the differentiation and proliferation of hematopoietic progenitor cells and of activating certain mature cells of the hematopoietic system. Thus, the G-CSF obtained by means of the method according to the present invention is suitable for treating indications where administration of G-CSF is advantageous. It is understood that the term "biologically active human G-CSF" also includes mutants and modifications of G-CSF, whose amino acid sequences are altered as compared to the wild type sequence, but which have similar biological activities as the wild type G-CSF. The same applies to G-CSF conjugates. Typically, the G-CSF is human recombinant G-CSF. Preferably, the G-CSF to be purified is human methionyl (Met) G-CSF produced in *E. coli* cells.

The term "a less hydrophobic isoform", as used herein, refers to a G-CSF preparation/fraction which has the same mass, isoelectric point and identical peptide mapping including disulfide bridges as revealed for example by Edman degradation and Isoelectric Focusing (IEF) gels or by mass spectrometry. Moreover, neither lipid-adducts nor iso-aspartate are detectable by mass spectrometry. The less hydrophobic G-CSF isoform can be characterized in its difference in CD-spectra compared to G-CSF reference in the near UV-range (OD 260-320 nm) indicating a higher content of α-helical structures (66% for the isoform and 52% for the G-CSF reference). In addition, the difference in hydrophobicity of the subject G-CSF and its isoform can be demonstrated by analytical RP-HPLC at 60° C. These differences are the reason why the less hydrophobic isoform is eluted in an earlier fraction compared to the G-CSF reference in a RP-HPLC chromatography, which is applied at 60° C. Thus, the G-CSF isoform according to the invention can be defined by its distinct properties of being less hydrophobic and eluting in a RP-HPLC applied at 60° C. in different fractions, wherein the G-CSF isoform is eluted prior to the main peak of the subject G-CSF; see FIG. 3. Techniques to characterize the samples comprised SDS-PAGE, IEF, UV, CD, fluorescence spectroscopy and NMR; see also supra and the Examples. Taken all information together, the less hydrophobic G-CSF isoform is best explained as a folding variant having a slightly altered 3D structure, which is regarded as a misfolded form. Its removal should lead to more efficient and safe drug products.

As mentioned, the G-CSF preparation of the present invention is substantially free of the less hydrophobic G-CSF isoform. The term "substantially free" of a less hydrophobic G-CSF isoform or "with a minimized amount" of the less hydrophobic G-CSF isoform means that the G-CSF preparation of the present invention typically contains less than 5% of the less hydrophobic G-CSF isoform, preferably less 1%, advantageously less than 0.2% of the less hydrophobic G-CSF isoforms.

According to the present invention, the term "inclusion bodies" refers to intracellular insoluble, compact aggregates from incorrectly folded or partially correct folded recombinant expressed protein, which can be isolated as a particulate fraction by centrifugation of cell lysates.

The term "solubilization" as used herein means that G-CSF which forms inclusion bodies becomes dissolved by treating with a denaturant, e.g., a chaotropic agent and a reducing agent, whereby inter- and intramolecular interactions, which are not present in the naïve protein, become broken, thereby resulting in a monomeric dispersion of recombinant G-CSF.

According to the present invention, the term "denaturing agent" refers to an agent, which is able to defold a protein, thus resulting in a reduction or loss of the native protein conformation. For the use in solubilization buffers, suitable chaotropic agents or denaturants are urea, guanidine-HCL, arginine, sodium thiocyanant, pH-extreme (diluted acidic or bases), detergents (e.g. SDS, Sacrosyl), salts (chloride, nitrates, thiocyanates, trichloroacetate), chemical derivatization (sulfitolyse, reactions on the bases with Citraconanhydrid), solvents (2-amino-2-methyl-1-propanol or alcohols, DMSO, DMS) or strong anion exchange resins as for instance Q-Sepharose.

Appropriate concentrations of urea are 1-9 mol/l, preferably 5-9 mol/l. Appropriate concentrations of guanidine-HCl are 1-8 mol/l, preferably 4-8 mol/l. In a preferred embodiment according to the present invention, the denaturing agent is guanidine-HCl, preferably wherein the concentration of guanidine-HCl is 6.0 mol/l; see also the Examples.

Typically, the solubilization buffer in the method of the present invention contains a reducing agent in addition to the denaturing agent. Suitable reducing agents are reduced glutathione (GSH), dithiothreitol (DTT), dithioerythritol (DTE), cysteine, β-mercaptoethanol. Preferably, the reducing agent in the method of the present invention is DTT. In one embodiment of the present invention, the concentration of the reducing agent in the solubilization buffer is 1 to 100 mmol/l, preferably 1 to 10 mmol/l, and may be adjusted in accordance with the Examples. According to the present invention, a suitable buffer component of the solubilization buffer can be tris(hydroxymethyl)-aminomethane or phosphate, which should exhibit a basic pH value, in order to allow the reduction of disulfide bridges.

In order to ensure an efficient and complete solubilization, an appropriate ratio of inclusion bodies and solubilization buffer is required. According to the present invention, 10 to 100 ml of solubilization buffer per gram of inclusion bodies are used, preferably 1 to 80 ml, most preferably 1 to 40 ml, more preferably >20 ml/g and typically >30 ml per gram inclusion body.

Furthermore, in one embodiment of the present invention a chelating agent, for instance ethylene diamine tetra acetate (EDTA) or dimethylaminoethanol (DMAE) is added to the solubilization and/or refolding buffer to complex metal ions in aqueous solution. Once bound to EDTA, these metal ions tend not to interfere with the action of the detergents or have the ability to oxidize the reducing agent. In addition, metal-dependent proteases are inhibited by the chelating agents. In a preferred embodiment of the present invention the solubilization buffer and/or refolding buffer contains di-sodium EDTA, preferably in a concentration between 0.5 to 10 mM.

According to the present invention, to ensure an efficient and complete solubilization, the solubilization time in the method of the present invention is 1 to 10, preferably 4 to 8, most preferably 6±1 hours or 5.5 to 6.5 hours. In a further preferred embodiment the solubilization process is carried out at ambient temperatures above 10° C., preferably between 15-30° C., most preferably at 20±2° C., i.e. at the same or similar temperature as the refolding process; see supra and the Examples.

According to the present invention, host cell debris should be eliminated from the solubilized G-CSF to ensure that no distracting substances interfere with the refolding process. Therefore, the solubilizate is preferably subjected to filtration prior to diluting with the refolding buffer. For example, solubilized G-CSF protein is separated from host cell debris, aggregated unfolded protein, dimers, multimers and/or unfolded protein of G-CSF by filtration through a 1.5 µm filter.

Intramolecular disulfide bond formation in G-CSF protein is promoted by the addition of a refolding buffer comprising a redox couple. A "redox couple" refers to mixtures of reduced and oxidized thiol reagents and include for instances reduced and oxidized glutathione (GSH/GSSG), cysteine/cystine, cysteamine/cystamine, DTT/GSSG, and DTE/GSSG as well as mixtures of any one of the mentioned redox couple components; see, e.g., Clark, Cur. Op. Biotech. 12 (2001), 202-207. In one embodiment of the present invention, the redox couple is GSH/GSSG, wherein the concentration of reduced and oxidized glutathione is 0.1 to 20 mmol/l, preferably 0.5 to 10 mmol/l, most preferably 0.2 to 10 mmol/l each; see also the Examples.

Refolding in order to achieve biologically active G-CSF can be performed in buffers at a neutral or basic pH. Preferably, the refolding process is performed at a pH value of about 8. Refolding buffers can include other additives to enhance refolding, e.g., L-arginine or arginine hydrochloride (0.4-1 mol/l); PEG; low concentrations of denaturants such as urea (1-2 mol/l) and guanidine-HCl (0.5-1.5 mol/l); and detergents (e.g., Chaps, SDS, CTAB, lauryl maltoside, Polysorbate 80/Tween 80©, and Triton X-100). In one preferred embodiment of the present invention, the refolding buffer further contains arginine-HCl.

Among the known refolding strategies, dilution is still the simplest methodology. In industrial scale applications, dilution is commonly used for refolding of recombinant proteins expressed in inclusion bodies. Typically, dilution is carried out in one step by mixing/diluting the solution containing solubilized protein with a diluent containing a solubilizing agent in an amount necessary to reach the optimal level of dilution. When the concentration of solubilizing agent is below a certain threshold level, the protein starts to regain its biologically active three-dimensional conformation. Depending on the specific protein and the chosen folding conditions, refolding begins within milliseconds to seconds. In this initial burst phase, the protein is highly susceptible to aggregation. To minimize aggregation, the protein concentration has to be kept rather low, preferably below 2 mg/ml. After this initial refolding phase, the protein forms into a more compact structure and finally, to native protein conformation that is less susceptible to aggregation. Complete refolding, including formation of disulfide bonds, can be achieved for G-CSF within hours. In order to ensure an efficient and complete renaturation, an appropriate ratio of solubilizate with refolding buffer is required. According to the present invention, the solubilizate is diluted with refolding buffer in a ratio of 1 to 100, preferably 1 to 40, most preferably 1 to 20; see also the Examples.

The term "diluting with refolding buffer" as used in accordance with the method of the present invention in principle includes diluting the solubilizate into a predetermined amount of refolding buffer and pouring the refolding buffer into the solubilizate sample. Preferably, the solubilizate is added to the refolding buffer under stirring. In a preferred embodiment of the present invention, the dilution process lasts about one hour.

As mentioned above, in the method of the present invention the refolding process in a suitable redox system can be conducted at ambient temperatures, i.e. usually above 10° C. within less than half a day and advantageously at room temperature, i.e. at 20±2° C. within 3 to 4 hours. The ambient temperature may vary between 10° C. and 30° C. and is preferably between 15° C. and 25° C., more preferably between 17° C. and 23° C. and particularly preferred between 19° C. and 21° C. The time for refolding may be oriented towards the conditions illustrated in the Examples. Thus, while the refolding process at about 20±2° C. lasts about 3 to 4 hours either the same time frame or one or two hours more or less may be used dependent on whether the refolding process is carried out below 18° C. or above 22° C. In any case, the duration of the refolding process is less than 12 hours.

Using the method of the present invention, 70% of the total G-CSF protein content from inclusion bodies can be refolded into biologically active G-CSF.

The refolding process can be stopped by lowering the pH of the refolding buffer to an acidic pH. In one preferred embodiment of the present invention, acetic acid is used to reduce the pH to 3.0 to 6.5, preferably to 3.5 to 5.5, most preferably to 4.0.

Once the G-CSF protein has been refolded, a tenside or surfactant may be added to the protein sample. In a preferred embodiment of the present invention, a non-ionic detergent, preferably Polysorbate 20 or 80, most preferably Polysorbate 80 (Tween 80©) is added to the sample of the refolded G-CSF protein in a final concentration of 0.001 to 1%, preferably 0.05 to 0.1%, most preferably at a final concentration of 0.05 to 0.06% or of 0.01%, depending on the further use of the G-CSF.

In many cases, it will be advantageous to subject the refolding setup to filtration prior further processing in order to remove high-molecular particles, which are often protein aggregates formed during folding. In one preferred embodiment of the method of the present invention, the refolded protein solution is filtered through a filter cascade, preferably through a 10 and 1.2 µm filter cascade. Following filtration, the solution can be stored in a holding step, wherein ambient temperatures like 22±2° C. are preferred; see also FIG. 1 and Table 1 in appended Example 6 of the present invention.

In order to achieve higher product concentration of the G-CSF preparation obtained after refolding, the G-CSF protein can be dialyzed or diafiltrated to remove the redox couple and/or other unwanted buffer components. Accordingly, a filtration process is provided herein to remove cell debris, insoluble contaminating proteins and nucleic acid precipitate. This step provides a convenient means to economically remove cell debris, contaminating proteins and precipitate. In choosing a filter or filter scheme, it is necessary to ensure a robust performance in the event upstream changes or variations occur. Maintaining the balance between good clarification performance and step yield requires investigation of a large variety of filter types with various filter media. Suitable filter types may utilize cellulose filters, regenerated cellulose fibers, cellulose fibers combined with inorganic filter aids (e.g. diatomaceous earth, perlite, fumed silica), cellulose fibers combined with inorganic filter aids and organic resins, or any combination thereof, and polymeric filters (examples include but are not limited to nylon, polypropylene, polyethersulfone) to achieve effective removal. In one embodiment, filtration e.g. an ultra and a diafiltration step is conducted using a 5-10 kDa UF membrane and an about 8× buffer exchange where the buffer is exchanged by Na-acetate and a non-ionic detergent, e.g., Polysorbate 80 at a pH 4.

Diafiltration is a fractionation process of washing smaller molecules through a membrane, leaving the larger molecule of interest in the retentate. It is a convenient and efficient technique for removing or exchanging salts, removing detergents, separating free from bound molecules, removing low molecular weight materials, or rapidly changing the ionic or pH environment. The process typically employs a microfiltration membrane in order to remove a product of interest from slurry while maintaining the slurry concentration as a constant.

As described above, the essential chromatographic purification step in the method of the present invention comprises reversed phase (RP) chromatography, in particular a reversed phase-high pressure liquid chromatography (RP-HPLC) step at an industrial scale. By analytical RP-HPLC at 60° C., it is possible to visualize the less hydrophobic G-CSF isoform contaminant in the G-GSF sample obtained after the refolding process, which is characterized by the α-helical content of 66% and the elution profile shown in FIG. 3. As mentioned in the prior art, different ion exchange or hydrophobic chromatography steps have been performed to purify G-CSF, while RP-HPLC as a purifying step at an industrial scale has not been envisaged.

Means and methods for performing reversed phase (RP) chromatography are well known to the person skilled in the art. Preferably, the reversed phase (RP) chromatography step is reversed phase-high pressure liquid chromatography (RP-HPLC). Typically, the RP-HPLC is performed with resins that contain Methyl-, Butyl-, Phenyl-, Propyl- and/or Octyl-groups as functional groups and employing organic solvent containing mobile phase systems. In a preferred embodiment of the method of the present invention, the RP-HPLC is performed with a commercially available C4 reversed phase chromatography material. Exemplary reversed phase materials are: Vydac 214TPB1015, C4 available from Grace Davison; Daisopak SP-300-15-C4-BIO available from DAISO Fine Chem. GmbH; YMC Gel Butyl Sphärisch C4, 15µ, 300 A available from YMC Europe GmbH; Jupiter 15µ, C4, 300 A available from Phenomenex.

In a particularly preferred embodiment of the method of the present invention, a Jupiter C4 chromatographic resin is used in the RP-HPLC and a Source 15 RPC or Source 30 RPC chromatographic resin (supplier GE Healthcare) is used in the RP chromatography. Jupiter C4 consists of silica gel particles, the surfaces of which carry C4-alkyl chains. According to the present invention, a Jupiter C4 chromatographic resin is most preferably used; see also the Examples.

The separation of G-CSF from the proteinaceous impurities is based on differences in the strength of hydrophobic interactions. Elution is performed with a less polar solvent than water, e.g., an acetonitrile, ethanol or methanol gradient in water, preferably using acetonitrile in presence of diluted trifluoroacetic acid. Thereby, the less hydrophobic isoform of G-CSF can be separated from G-CSF by being eluted within different fractions. Usually, the less hydrophobic isoform of the total G-CSF preparation is eluted in an earlier fraction than the G-CSF standard. G-CSF and the less hydrophobic G-CSF isoform may be eluted with a linear gradient of an organic solvent, for example from 0 to 90% acetonitrile in water, i.e. Water for Injection (WFI) and containing about 0.1% TFA. Preferably, the RP-HPLC is carried out as described in the Examples. The eluate is preferably collected in vials prefilled with buffer containing Polysorbate 80; see also supra and the Examples.

As explained above and illustrated in the Examples, in the method of the present invention the RP chromatography step is typically preceded by an ion exchange chromatography. Thus, in a preferred embodiment of this invention, G-CSF is purified using single ion-exchange chromatography in order to remove all the contaminants like host cell proteins, in particular endotoxins and host cell DNA. In principle, cation exchange chromatography or anion exchange chromatography may be used.

In a particularly preferred embodiment of the method of the present invention, a cation exchange chromatography (CEX) is carried out after the refolded G-CSF is ultra- and diafiltrated. As illustrated in the Examples, a CEX chromatography step with a selected material (CM Sepharose® FF) is being performed that allows particularly high flow rates and good product recovery. Due to the fact that it is positively charged in an acidic environment, G-CSF is a strong binder and is eluted with a linear sodium chloride gradient at an acidized pH in a small volume at a high concentration in the desired buffer. Thus, in accordance with the present invention the CEX step is used before RP chromatography, in particular before a RP-HPLC, for buffer exchange, concentration of G-CSF and removal of G-CSF aggregates. Means and methods for performing cation exchange chromatography are well known to the person skilled in the art; see also the prior art recited in the background section, supra or the supplier GE Healthcare. For example, conventional commercially available matrices can be employed. Herein, the G-CSF binds to the cation exchange matrix within a specific pH range due to its positive total charge, while most of the contaminating substances like nucleic acids, lipopolysaccharides and proteins originating from host cells as well as ionic isomers of G-CSF and altered forms of G-CSF having different pH values are not capable of binding and appear in the flow-through or are of being removed by means of washing. Suitable cation exchange matrices include, but are not limited to, carboxymethyl (CM) cellulose, AG 50 W, Bio-Rex 70, carboxymethyl (CM) Sephadex, sulfopropyl (SP) Sephadex, carboxymethyl (CM) sepharose CL-6B, CM sepharose HP, Hyper D-S ceramic (Biosepra) and sulfonate (S) Sepharose, SP Sepharose FF, SP Sepharose HP, SP Sepharose 15 XL, CM Sepharose FF, TSK gel SP 5PW, TSK gel SP-5PW-HR, Toyopearl SP-650M, Toyopearl SP-650S, Toyopearl SP-650C, Toyopearl CM-650M, Toyopearl CM-650S etc. Sulfopropyl matrices, in particular the products SP Sepharose XL and SP Sepharose FF (Fast Flow) and S-Sepharose FF, available by Amersham Biosciences, Freiburg, Germany (now GE Healthcare). In one embodiment, the cation exchange material is a sulfopropyl cation exchange material. In a preferred embodiment of the method of the present invention ion-exchange chromatography is cation exchange chromatography (CEX) and is performed with CM-Sepharose FF; see also the Example 6 and 7.

Suitable buffers for the cation exchange chromatography include maleate, malonate, citrate, lactate, acetic acid, acetate, phosphate, REPES, Bistris and Bicin buffers. In a preferred embodiment acetic acid as a buffer component is used. Preferably, the concentration of the buffer lies between 10 and 100 mM, preferably between 20 mM and 50 mM. According to the present invention a tenside is also included in the buffer, preferably Polysorbate 20 or 80, most preferably Polysorbate 80 is used; see also supra. Purifying the G-CSF preparation is conducted by the use of a pH value of the buffer not be higher than 6.0, preferably not higher than 5.5. Subsequently washing of the column wherein G-CSF is bound is usually performed by five column volumes (CVs) of equilibration buffer, composed of acetic acid, Polysorbate 80 at pH 5.5.

G-CSF can be eluted from the column by means of an alteration of the buffer, in case of the cation exchange chromatography by means of an increase in pH value or an increase in ionic strength. Preferably, the elution is effected by means of increasing the ionic strength, preferably by using a linear sodium chloride gradient. Suitable conditions for the cation exchange chromatography can be taken from the relevant literature, like for example from the manual "Ion Exchange Chromatography—Principles and Methods" by Amersham Biosciences, Freiburg, Germany (now GE Healthcare), 2002 and Example 7.

In a particular preferred embodiment the method of the present invention, the purification process comprises:
(i) an ultra-/diafiltration step;
(ii) a cation exchange (CEX) chromatography step:
(iii) a microfiltration step;
(iv) a reversed phase (RP) chromatography step; and
(v) an ultra-/diafiltration step.

Figure 1:
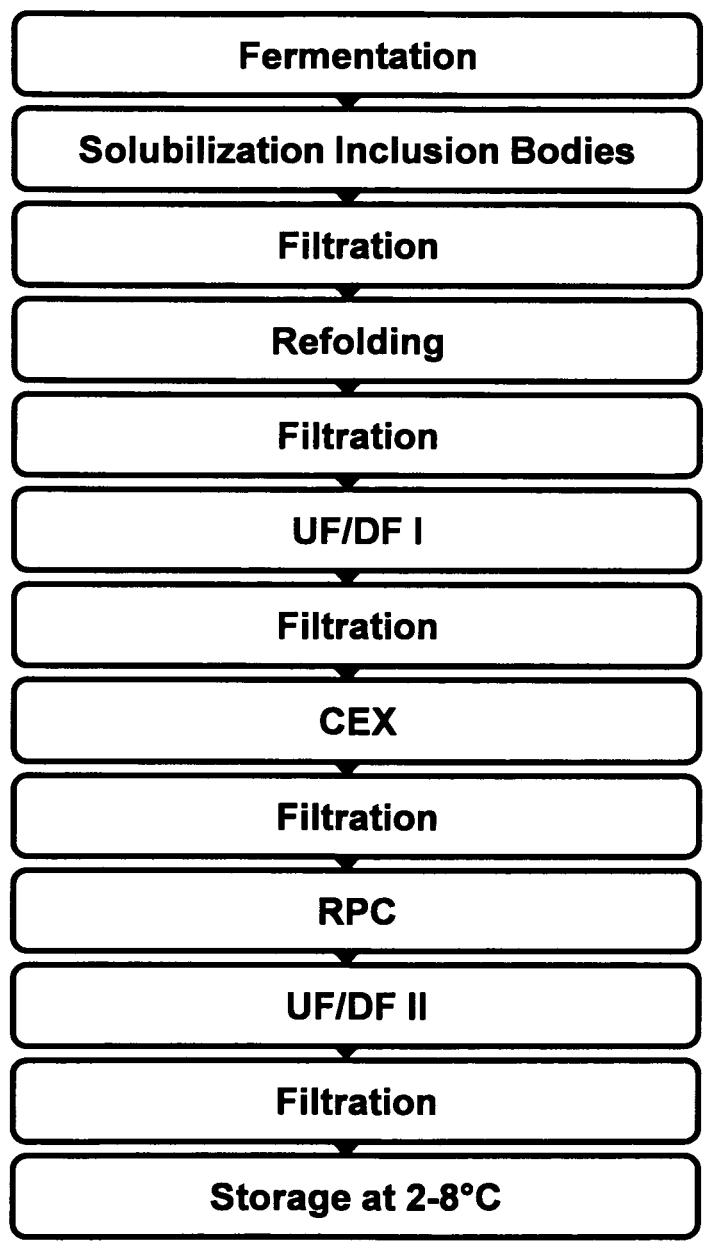
FIG. 1: Flow chart scheme illustrating isolation and purification procedure of G-CSF according to the method of the present invention. As illustrated, in one preferred embodiment of the present invention, the process of purification and obtaining biologically active human G-CSF from inclusion bodies comprises the steps.

This embodiment is also shown in FIG. 1 and illustrated in the Examples. In the first (i) step the ultra-/diafiltration the buffer is exchanged by Na-acetate, Polysorbate 80 at an acid pH. Finally, the solution is filtered through a 10 and 1.2 μm filter cascade. Following filtration, the solution can be stored at 22±2° C. (hold step). Chromatographic purification steps are designed to remove cell culture components, bacterial cell impurities and process- and product-related impurities and to ensure consistent G-CSF content for further processes. The enrichment of highly purified G-CSF in accordance with the present invention is carried out in the subsequent filtration and chromatographic steps; see also FIG. 1. In a further embodiment of the method of the present invention, the G-CSF preparation obtained from step (ii) cation exchange chromatographic (CEX) is subjected to a microfiltration step (iii) wherein soluble impurities are removed from cell homogenate. In order to achieve a pure G-CSF preparation without the less hydrophobic isoform, step (iv), the RP-HPLC is further performed. Subsequently, a final ultra/diafiltration step is used as final polishing step and to formulate the G-CSF into its desired buffer. This accommodates for the need to obtain a small final volume of the preparation, i.e., the concentration of G-CSF in the RP-HPLC pool has to be strongly increased, and to formulate the RP-HPLC pool into a suitable buffer to further stabilize the purified G-CSF.

After the different purification steps according to the present invention have been conducted, the G-CSF purity is high, reaching a purity exceeding at least 98% or even 99% of total protein, as determined by RP-HPLC and SDS-PAGE gel electrophoresis, respectively; see also FIG. 2. Moreover, the dimer/multimer content of the purified G-CSF preparation according to the present invention is typically <2%, preferably <1%, while the remaining contamination of host cell DNA is ≤100 ppm or ≤200 ppm of host cell protein, respectively. Furthermore, in one preferred embodiment, contamination by endotoxins is ≤5 EU/mg, the total bioburden is <1 CFU/10 ml. Moreover, the final content of remaining trifluoroacetic acid (TFA) and acetonitrile is ≤30 ppm and ≤410 ppm, respectively.

Due to the high purity and homogeneity of the G-CSF preparation obtained in accordance with the method of the present invention, the G-CSF preparation of the present invention is particularly suited for further derivatization. Therefore, in a further embodiment, the method of the present invention further comprises chemical modification of the G-CSF obtained in accordance with the said method, for example by covalently attaching a water-soluble polymer to the G-CSF such as polyethylene glycol (PEG). Polyethylene glycol (PEG) conjugation to proteins is an important technology to produce molecules with prolonged duration in the human body. Attachment of a 10- to 30-kDa PEG moiety to G-CSF can have the ability to (1) prevent protein precipitation by rendering the proteins more soluble, and (2) lower the rate of aggregation relative to G-CSF, due to the fact that PEG-G-CSF solubility is mediated by favorable solvation of water molecules around the PEG group.

The term "water-soluble" refers to moieties that have some detectable degree of solubility in water. Exemplary water-soluble polymers include peptides, saccharides, poly(ethers), poly(amines), poly(carboxylic acids) and the like. The polymer backbone of the water-soluble polymer can be poly(ethylene glycol) (i.e. PEG).

The term "water-soluble polymer" covalently attached to G-CSF refers to a conjugate between a G-CSF polypeptide and at least one polymer wherein the conjugates is formed by a covalent linkage between a functional group of the polymer and a functional group of the polypeptide. The conjugates may comprise one or more polymeric moieties. Several suitable polymeric moieties or polymers include poly(alkylen glycols), such as PEG and PPG, hydroxyalkyl starches, such as hydroxyethyl starch (HES). In a preferred embodiment, said water-soluble polymer is polyethylene glycol (PEG). Such Pegylated G-CSF include monopegylated G-CSF and G-CSF modified with two or more PEG molecules. In a further preferred embodiment, said covalently attached polymer is about 10 to 30 kDa, preferably 20 kDa. Methods of chemical modification of G-CSF, in particular pegylation are well known to the person skilled in the art and are described in, e.g., in WO2008/124406.

The present invention also relates to a preparation of G-CSF obtained by the method of the present invention as defined above. Thus, the G-CSF preparation of the present invention is particularly suited for therapeutic application. In this context, the present invention also relates to a process for the manufacture of a pharmaceutical composition, the process comprising preparing and isolating G-CSF as defined above, and providing a mixture of the thus prepared and isolated G-CSF with a pharmaceutically acceptable carrier.

A preferred embodiment is a method for the production of a pharmaceutical composition of recombinant G-CSF and pharmaceutically acceptable additives such as buffers, salts and stabilizers, wherein said method comprises the method for obtaining G-CSF of the present invention as described above. The G-CSF obtained according to the present invention can either be (i) used directly or (ii) further processed, for instance pegylated as defined above or see WO2008/124406 and then stored in the form of a lyophilisate or in liquid form.

The G-CSF as an active ingredient of a pharmaceutical composition may be administered in a typical method through an intravenous, intra-arterial, intraperitoneal, intrasternal, transdermal, nasal, inhalant, topical, rectal, oral, intraocular or subcutaneous route. The administration method is not particularly limited, but a non-oral administration is preferable, and the subcutaneous or intravenously administration is more preferable.

Suitable adjuvants in the formulations of the recombinantly expressed G-CSF are, for example, stabilizers like sugar and sugar alcohols, amino acids and tensides like for example Polysorbate 20/80 as well as suitable buffer substances. For further embodiments of G-CSF formulations of the present invention see, e.g., WO2009/027437 and WO/2008/124406, the disclosure content of which is incorporated herein by reference. Examples for formulations see also the trade products Neupogen® and Granocyte in the "ROTE LISTE 2004". In a preferred embodiment according to the method of the present invention, the purified biologically active G-CSF is formulated in 10 mM acetic acid at a pH of 4.0, 0.0025% Polysorbate 80 and 50 g/l Sorbitol.

The activity of the G-CSF obtained according to the method of the present invention can be determined by means of a bioassay and compared with the activity of a standard, commercially available G-CSF. To this end, the mouse cell line NFS-60, which is responsive to G-CSF is cultivated in RPMI 1640 medium (Bachern, Heidelberg, Germany), which contains 1.5 g/l sodium carbonate, 4.5 g/l glucose, 10 mM Hepes and 1.0 mM sodium pyruvate and supplemented with 2 mM glutamine, 10% FCS, 0.05 mM 2-mercaptoethanol and 60 ng/ml G-CSF. For the activity test, the cells are washed twice with medium without G-CSF, placed in 96-well plates at a concentration of $2 \times 10^4$ cells per well and incubated for three days at 37° C. and 4.5% $CO_2$ with varying concentrations of the purified G-CSF and the standard, respectively. Subsequently, the cells are stained with XTT reagent and the absorption at 450 nm is measured in a microtiter plate reader.

In according to the present invention it could be shown that cells treated with the G-CSF purified according to the present invention grow just as well or better as those cells that are treated with the standard. In particular, the data show that purified G-CSF obtained according to the method of the present invention is characterized by a biological activity of 80-125% referring to WHO-reference standard in the NFS-60 proliferation assay.

Pharmaceutical compositions of the present invention are characterized as being sterile and pyrogen-free. As used herein, "pharmaceutical composition" includes formulations for human and veterinary use. Methods for preparing pharmaceutical compositions of the invention are within the skill in the art, for example as described in Remington's Pharmaceutical Science, 17th ed., Mack Publishing Company, Easton, Pa. (1985) and update version Remington: The Science and Practice of Pharmacy (2000) by the University of Sciences in Philadelphia, ISBN 0-683-306472, the entire disclosure of both documents which is incorporated herein by reference.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples, which are provided herein for purposes of illustration only and are not intended to limit the scope of the invention. In particular, the Examples relate to preferred embodiments of the present invention.

EXAMPLES

Unless defined otherwise, all technical and scientific terms used herein have the same meaning as commonly understood by one of ordinary skill in the art (e.g., molecular genetics, nucleic acid chemistry, hybridization techniques, protein chemistry and biochemistry). Standard techniques are used for molecular, genetic and biochemical methods (see generally, Sambrook et al., Molecular Cloning: A Laboratory Manual, $2^{nd}$ ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc.—and the full version entitled Current Protocols in Molecular Biology, which are incorporated herein by reference) and chemical methods.

Example 1

Starting Material

G-CSF is expressed in 03-221C-pHIP, an expression vector derived from pBR322. The E. coli host strain BNN93 was transformed with this plasmid for production. BNN93 is an E. coli K12 derivative. G-CSF synthesis is regulated by a lambda promoter, which is induced by a temperature shift from 30° C. to 42° C., resulting in the over-expression of primary insoluble G-CSF in inclusion bodies.

Example 2

Fermentation

The content of one vial of Working Cell Bank (WCB) diluted with 1,000 mL of complex medium without kanamycin is used to generate the "diluted working cell bank" for pre-fermentation. Dilution takes place in a laminar airflow hood (LAF) grade A in a clean room grade B. The pre-culture is aseptically transferred directly into the 20 L pre-fermenter. The culture is initiated at 30±1° C. with 250 rpm agitation for 6 to 12 hours until it reaches $OD_{600}$ 0.3 to 0.6. The complete fermentation broth is transferred into a 1,000 L fermenter pre-filled with complex medium without kanamycin. The culture is incubated at 30±1° C. with agitation ≥200 rpm to assure a $pO_2$≥30% and pH 7.0±0.2, for 9 to 11 hours until an $OD_{600}$ of 5 to 7 is reached.

Example 3

G-CSF Expression in Inclusion Bodies

Expression of G-CSF is induced by increasing the temperature to 42° C. and further incubation for 6.75 to 7.25 hours with agitation at ≥200 rpm to assure a $pO_2$≥30%. The bacterial cells are harvested at room temperature by a disk separator at 150 L/h, resulting in around 100 L concentrated cell suspension.

Example 4

Isolation of Inclusion Bodies

The concentrated cell suspension is diluted to 200 L and homogenized at 500 bar by three subsequent passages in 20 mM Na-phosphate, pH 8.0 with 300 L/h using a high pressure homogenizer. The released inclusion bodies are subsequently harvested by tubular bowle centrifugation at 17,000 rpm with 50 L/h. Following a resuspension in 18 mM Na-phosphate, 2% (w/v) Triton X-100, 5 mM EDTA, pH 8.0 for 10 minutes, the inclusion bodies are centrifuged again at 17,000 rpm with 50 L/h. The resulting pellet is washed with 18 mM Na-phosphate pH 8.0 for 10 minutes followed by another centrifugation at 17,000 rpm with 50 L/h. The pellet is resuspended in Water For Injection (WFI) and dispensed into three equal aliquots. The inclusion bodies are then stored at <−15° C. (hold step).

Example 5

Solubilization of Inclusion Bodies and Refolding of G-CSF

After thawing one third of the total inclusion body amount derived from a 1,000 liter fermentation, inclusion bodies are solubilized by incubation in 25 mM Tris, 6 M GuHCl, 1 mM EDTA, pH 8.0 for 5.5 to 6.5 hours with stirring, followed by filtration with a 1.5 filter, e.g., depth filtration (clarification filtration). The G-CSF is then refolded by dilution in 25 mM Tris, 0.8 M arginine, 1 mM glutathione (reduced) 1 mM glutathione (oxidized), 10 mM EDTA, pH 8.0 at 20±2° C. This is followed by addition of Polysorbate 80 to a final concentration of 0.01% (w/v) and adjustment to pH 4.0 with acetic acid. Following refolding, an ultrafiltration and a diafiltration step are conducted (MWCO 10 kDa, 8.4 $m^2$, approximately 8× buffer exchange) where the buffer is exchanged by 10 mM Na-acetate, 0.01% (w/v) Polysorbate 80, pH 4.0. Finally, the solution is filtered through a 10 and 1.2 μm filter cascade. Following filtration, the solution is stored at 22±2° C. (hold step).

Example 6

G-CSF Purification

Chromatographic purification steps are designed to remove cell culture compounds, bacterial cell impurities, process- and product-related impurities, and to ensure consistent G-CSF content for the preparation of a pharmaceutical formulation or for subsequent pegylation; see the following Examples. An outline of the process of the present invention is given in FIG. 1 and described in Table 1 below. A more detailed description carrying out the cation exchange and RP-HPLC chromatography is provided by Example 7 in Table 2 and 3.

TABLE 1

Buffer compositions used in the indicated process steps.

| Process steps | Buffer/solution |
|---|---|
| Homogenization | |
| Homogenization puffer | 20 mM Sodium-Phosphate, pH 8.0 |
| Homogenization press | 500 bar |
| Solubilization of IBs | |
| Solubilizationbuffer | 25 mM Tris, pH 8.0, 6M Guanidin-HCl; 1 mM Titriplex III Addition of DTT ad 5 mM; |
| mL Solubilization buffer/per Gram IBs | 38.25 mL Solubilizationbuffer/g IBs (1166 ± 12 g IBs + 44.6 L Solu-Puffer) |
| Duration | 5.5-6.5 h |
| Temperature | 20 ± 2° C. |
| Stirring | 200 rpm propeller stirrer in a mobile tank |
| Depth filtration | 1.5 µm pore size |
| Refolding | |
| Refolding buffer | 25 mM Tris, pH 8.0, 0.8M Argininhydrochloride, 10 mM Titriplex III Additive: 1 mM GSSG; 1 mM GSH |
| Dilution Refoldingbuffer | Approx. 1 + 19 (e.g. independent of total protein content) (approx. 47 L IB-supension + 19 parts Refolding buffer, i.e. 894 ± 9 L) |
| Dosage time of solubilized IB suspension | within 50-70 min. |
| Duration after dosage | 3.5-4.5 h |
| Temperature | 20 ± 2° C. |
| Stirring | 200 rpm propeller stirrer |
| Addition of Polysorbate 80 | ad 0.01% |
| Stop of refolding | Titration ad pH 4.0 with 50% HAc |
| Filtration | 10 µm and 1.2 µm Filtration |
| Ultra-/Diafiltration | |
| Membrane buffer | Hydrosart, 10 kDa buffer: 20 mM acetic acid, pH 4.0, 0.01% (w/v) Polysorbate 80 |
| Chromatography 1 | |
| Resin | CM-Sepharose FF, pH 5.5 Puffer A: 20 mM acetic acid, pH 5.5, 0.004% (w/v) Polysorbate80 Puffer B: 20 mM acetic acid, pH 5.5, 0.004% (w/v) Polysorbate80, 350 mM NaCl |
| Filtration | 0.45 and 0.2 µm filtration |
| Chromatography 2 | |
| Resin | Jupiter C4 Reversed-Phase Resin Puffer A: 89% WFI, 0.1% TFA, 10% Acetonitrile Puffer B: 9% WFI, 90% Acetonitrile, 0.1% TFA Elution into 20 mM acetic acid, pH 4.0; 0.0025% (w/v) Polysorbate 80 |
| Ultra-/Diafiltration | |
| Membrane buffer | Hydrosart, 5 kDa Buffer: 10 mM acetic acid, pH 4.0; 0.0025% Polysorbate 80, 50 mg/ml sorbitol |
| Dilution to 1 mg/ml, double sterile filtration and bottling | Bag: 50 L 3D Thermo Fischer AF-Film/LDPE |

Example 7

Cation Exchange Chromatography and Reversed Phase-High Pressure Liquid Chromatography The diafiltered concentrate is loaded onto a cation exchange (CM Sepharose® FF) column. After loading, the column is washed with five column volumes (CVs) of equilibration buffer (20 mM acetic acid, 0.004% (w/v) Polysorbate 80, pH 5.5), and the bound G-CSF is eluted from the CM column using a linear sodium chloride gradient into a bag containing 20 mM acetic acid, pH 5.5, 0.004% (w/v) Polysorbate 80 and approx. 50-80 mg/ml sorbitol. The elution profile is monitored by UV detection (280 nm, 260 nm and 215 nm) and the gradient is controlled by measuring the conductivity. The eluted G-CSF is identified according to conductivity and absorbance profile. The concentration of the G-CSF pool fraction is determined by UV280 absorbance and diluted to ≤1.6 mg/mL.

TABLE 2

Parameter for performing Cation Exchange Chromatography: CM sepharose ®-FF
Cation Exchange Chromatography: CM sepharose ®-FF

| Parameter | Criterion |
|---|---|
| Resin | CM Sepharose ® FF (GE Healthcare) |
| Column device | Millipore QuickScale ® |
| Column diameter | 30 cm |
| Bed height | 11.0 + 1.0 cm |
| Theoretical plates | >7,500 N/m |
| Asymmetry factor | n.a. |
| Flow rate | 70.7 L/hr (100 cm/h) - all stages |
| Loading buffer | 20 mM acetic acid, pH 5.5; 0.004% (v/w) Polysorbate80 |
| Elution buffer | 20 mM acetic acid, pH 5.5; 0.04% (v/w) Polysorbate80, 350 mM NaCl |
| Elution volume | 1.4-1.7 CV |
| Elution/collection | Linear gradient 0-100% B in 7CV |
| Pooling criteria | Start 1.8 $AU_{280}$; Stop 0.5 $AU_{280}$ |

After filtration with a 0.45-0.22 µm filter unit, the solution is applied to an RP-HPLC column and fractions are eluted using an acidified (TFA) acetonitrile gradient in water. The elution profile is monitored by UV detection (280 nm). The RP-HPLC pool is defined on analytical RP-HPLC (at 60° C.) purity data and the pool is ultrafiltrated and diafiltrated by tangential flow filtration with 10 mM acetic acid, 0.0025% (w/v) Polysorbate 80, 50 mg/ml Sorbitol, pH 4.0 (MWCO 5 kDa, 4.8 m², approximately 8× buffer exchange).

TABLE 3

Parameter for performing Reversed Phase Chromatography: Jupiter C4
Phase Chromatography: Jupiter C4

| Parameter | Criterion |
|---|---|
| Resin | Jupiter ® C4, 300 Å (Phenomenex) |
| Column device | Stainless steel column (Peak Biotech) |
| Column diameter | 25 cm |
| Bed height | 25 ± 2.5 cm |
| Theoretical plates | n.a. |
| Asymmetry factor | n.a. |
| Colum temperature | 22 ± 2° C. |
| Flow rate | 98.1 L/hr (299 cm/h) - all stages |
| Loading buffer | 89% WFI/10% Acetonitrile, 0.1% TPA |
| Elution buffer | 9% WFI/90% Acetonitrile, 0.1% TPA |
| Elution volume | 1.7-2.0 CV |

TABLE 3-continued

Parameter for performing Reversed Phase Chromatography: Jupiter C4
Phase Chromatography: Jupiter C4

| Parameter | Criterion |
| --- | --- |
| Elution/collection | Elution I; Linear gradient 0-38% (24.5 L; 15.0 min) |
|  | Elution II: Linear gradient 38-72% (92.0 L; 56:3 min) |
|  | 7 x 1 L pre-fractions |
|  | 1 x 200 L main fraction |
| Pooling criteria | Start 0.02 $AU_{280}$; Stop 0.02 $AU_{280}$ |

Example 8

Filling, Storage and Transportation

The diafiltrate is diluted with the same buffer to a protein concentration of 1.0±0.1 mg/ml, then double-filtered (two 0.22 μm filters in a cascade) directly into one single use bag (pre filter connected to the final container in a LAF prior to filtration, final filter preassembled to the 50 L primary packaging bag, sterilized by irradiation and aseptically disconnected by sealing after filtration and filling) for storage at 5±3° C. (hold step).

The invention claimed is:

1. A method for obtaining biologically active human G-CSF from inclusion bodies comprising the steps:
   (a) solubilizing the G-CSF contained in the inclusion bodies with a solubilization buffer containing a denaturing agent and a reducing agent;
   (b) refolding the G-CSF by diluting the solubilizate with a refolding buffer containing reduced and oxidized glutathione at a temperature >10° C.; and
   (c) purifying the refolded G-CSF by a process comprising the steps:
      (i) an ultra-/diafiltration step;
      (ii) a CEX chromatography step;
      (iii) a microfiltration step;
      (iv) a RP chromatography step; and
      (v) an ultra-/diafiltration step.

2. The method of claim 1, wherein the denaturing agent is guanidine-HCl, preferably wherein the concentration of guanidine-HCl is 4.0 to 8.0 mol/l.

3. The method of claim 1, wherein the reducing agent is DTT.

4. The method of claim 1, wherein the concentration of the reducing agent in the solubilization buffer is 1 to 100 mmol/l.

5. The method of claim 1, wherein 10 to 100 ml of solubilization buffer per gram of inclusion bodies are used.

6. The method of claim 1, wherein the solubilization buffer and/or refolding buffer further contains a chelating agent.

7. The method of claim 1, wherein the solubilization time is 1 to 10 hours.

8. The method of claim 1, wherein the refolding buffer further contains arginine-HCl.

9. The method of claim 1, wherein the concentration of reduced and oxidized glutathione is 0.2 to 10 mmol/l each.

10. The method of claim 1, wherein the solubilizate is diluted with refolding buffer in a ratio of 1 to 20.

11. The method of claim 1, wherein refolding is carried out at 20±2° C. for at least 3 hours.

12. The method of claim 1, wherein the reversed phase (RP) chromatography step is RP high pressure liquid chromatography (RP-HPLC).

13. The method of claim 1, wherein the RP chromatography step is preceded by an ion-exchange chromatography.

14. The method of claim 1 further comprising covalently attaching a water-soluble polymer to the G-CSF.

15. The method of claim 14, wherein the molecular weight of the polymer is about 10 to 30 kDa.

16. A method for the production of a pharmaceutical composition of recombinant G-CSF and one or more pharmaceutically acceptable additive, wherein said method comprises the method for obtaining G-CSF of claim 1.

17. The method of claim 16, wherein the purified biologically active G-CSF is formulated in 10 mM acetic acid at a pH of 4.0, 0.0025% Polysorbate 80 and 50 g/l Sorbitol.

* * * * *